United States Patent
Li et al.

(10) Patent No.: US 10,392,352 B2
(45) Date of Patent: Aug. 27, 2019

(54) ETOMIDATE DERIVATIVE AND INTERMEDIATE, PREPARATION METHOD AND USE THEREOF

(71) Applicant: JIANGSU NHWALUOKANG PHARMACEUTICAL RESEARCH AND DEVELOPMENT CO., LTD., Xuzhou, Jiangsu (CN)

(72) Inventors: Qingeng Li, Chongqing (CN); Tao Wang, Chongqing (CN); Lingguo Zeng, Chongqing (CN); Guisheng Zhang, Xuzhou (CN); Xiangqing Xu, Xuzhou (CN); Liang Ren, Chongqing (CN)

(73) Assignee: JIANGSU NHWALUOKANG PHARMCEUTICAL RESEARCH AND DEVELOPMENT CO., LTD., Xuzhou (CN)

( * ) Notice: Subject to any disclaimer, the term of this patent is extended or adjusted under 35 U.S.C. 154(b) by 0 days.

(21) Appl. No.: 15/767,009

(22) PCT Filed: Oct. 10, 2016

(86) PCT No.: PCT/CN2016/101696
§ 371 (c)(1),
(2) Date: Apr. 9, 2018

(87) PCT Pub. No.: WO2017/059827
PCT Pub. Date: Apr. 13, 2017

(65) Prior Publication Data
US 2018/0297958 A1    Oct. 18, 2018

(30) Foreign Application Priority Data
Oct. 10, 2015 (CN) .......................... 2015 1 0650913

(51) Int. Cl.
*C07D 233/90* (2006.01)
*A61P 23/00* (2006.01)

(52) U.S. Cl.
CPC ............ *C07D 233/90* (2013.01); *A61P 23/00* (2018.01)

(58) Field of Classification Search
CPC .................................................. C07D 233/90
See application file for complete search history.

(56) References Cited

FOREIGN PATENT DOCUMENTS

| CN | 103739553 A | 4/2014 |
| CN | 104706587 A | 6/2015 |

OTHER PUBLICATIONS

Iddon et al. J. Chem. Soc. Perkin Tans. I. 1987, 1445-1451 (Year: 1987).*
"International Application No. PCT/CN2016/101696, International Search Report dated Jan. 9, 2017", w/ English Translation, (Jan. 9, 2017), 5 pgs.
"International Application No. PCT/CN2016/101696, Written Opinion dated Jan. 9, 2017", (Jan. 9, 2017), 3 pgs.
Cotten, Joseph F, "Methoxycarbonyl-etomidate A Novel Rapidly Metabolized and Ultra-short-acting Etomidate Analogue that Does Not Produce Prolonged Adrenocortical Suppression", Anesthesiology The Journal of the American Society of Anesthesiologists 111.2, (2009), 240-249.
Laha, Joydev K., "Synthesis of Fused Imidazoles, Pyrroles, and Indoles with a Defined Stereocenter a to Nitrogen Utilizing Mitsunobu Alkylation Followed by Palladium-Catalyzed Cyclization", The Journal of organic chemistry 76.20, (2011), 8477-8482.
"European Application Serial No. 16853130.9, European Search Report dated May 21, 2019", (May 21, 2019), 5 pgs.

* cited by examiner

*Primary Examiner* — Matthew P Coughlin
(74) *Attorney, Agent, or Firm* — Schwegman Lundberg & Woessner, P.A.

(57) ABSTRACT

The present invention discloses an etomidate derivative of Formula 1, or a pharmaceutically acceptable salt, a polymorph, or a solvate thereof, a pharmaceutical composition and a kit comprising the same, as well as intermediates and methods for preparing the same, and use thereof. The etomidate derivative of the present invention not only has good anesthetic activity, rapid onset, and short duration of action, but also shows little inhibition to the secretion of corticosteroids in animals, and therefore has both favorable anesthetic effect and safety profiles.

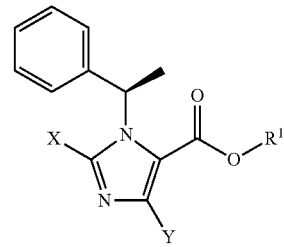

Formula 1

19 Claims, No Drawings

ETOMIDATE DERIVATIVE AND INTERMEDIATE, PREPARATION METHOD AND USE THEREOF

CROSS-REFERENCE TO RELATED APPLICATION

This application is a U.S. National Stage Filing under 35 U.S.C. 371 from International Application No. PCT/CN2016/101696, filed on Oct. 10, 2016, and published as WO2017/059827 on Apr. 13, 2017, which claims the benefit of priority from Chinese patent application No. 201510650913.2 filed on Oct. 10, 2015, the benefit of priority of each of which is hereby claimed herein, and which applications and publication are hereby incorporated herein by reference in their entirety.

TECHNICAL FIELD

The present invention relates to the field of pharmacy, specifically to an etomidate derivative, or a pharmaceutically acceptable salt, a polymorph, or a solvate thereof, a pharmaceutical composition and a kit comprising the same, as well as intermediates and methods for preparing the same, and use thereof.

BACKGROUND

"Etomidate", ethyl R-(+)-1-(1-phenethyl)-1H-imidazole-5-carboxylate, is an intravenous anesthetic drug with the characteristics of rapid onset, short duration of action, quick recovery, and slight inhibition to cardiovascular and respiratory systems. In clinical, etomidate is mainly used in anesthesia induction, and anesthesia for clinical surgery. The structure of etomidate is as follows:

Formula 4

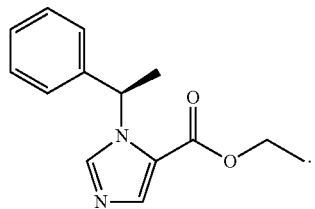

(etomidate)

However, researches have shown that while exerting the anesthetic effect, etomidate may have an inhibitory effect on 11β-hydroxylase, and thereby reduce the secretion of cortisol and/or corticosterone. Hence, there is a potential fatal risk in long term application of etomidate.

Extensive studies have been done by pharmaceutical chemists to overcome the disadvantages of etomidate and develop novel drugs which possess the advantages of etomidate without inhibiting the secretion of cortisol and/or corticosterone as strongly as etomidate. For example, Cotten J F et al. (Methoxycarbonyl-etomidate: A novel rapidly metabolized and ultra-short-acting etomidate analogue that does not produce prolonged adrenocortical suppression, *Anesthesiology*, 2009, 111: 240-9) reported an etomidate derivative of Formula 7, which shows a lower inhibitory effect on the secretion of cortisol and/or corticosterone, but has a drastically decreased anesthetic effect in the meantime. Similarly, Laha, Joydev K et al. (Synthesis of Fused Imidazoles, Pyrroles, and Indoles with a Defined Stereocenter α to Nitrogen Utilizing Mitsunobu Alkylation Followed by Palladium-Catalyzed Cyclization, *Journal of Organic Chemistry*, 2011, vol. 76, #20, p 8477-8482) disclosed a Carboetomidate-type etomidate derivative of Formula 8, which has little inhibition to the secretion of cortisol and/or corticosterone, but has decreased anesthetic activity and prolonged duration of action in the meantime.

Formula 7

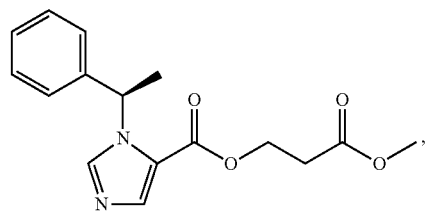

Formula 8

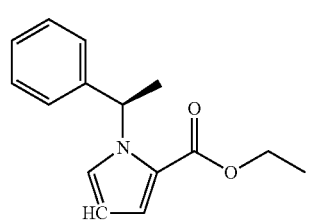

In view of the above problems, it has great practical significance to develop an etomidate derivative having both favorable anesthetic effect and safety profiles.

SUMMARY OF THE INVENTION

In a first aspect of the present invention, provided is an etomidate derivative, or a pharmaceutically acceptable salt, a polymorph, or a solvate thereof. The etomidate derivative of the present invention not only has good anesthetic activity, rapid onset, and short duration of action, but also shows little inhibition to the secretion of cortisol and/or corticosterone, and therefore has both favorable anesthetic effect and safety profiles.

The etomidate derivative of the present invention has the structure of Formula I:

Formula 1

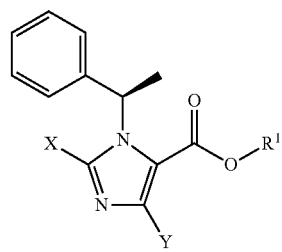

wherein,

X and Y are independently halogen or hydrogen, with the proviso that X and Y are not hydrogen at the same time; and $R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl.

In a second aspect of the present invention, provided is a pharmaceutical composition comprising the etomidate derivative of the present invention, or a pharmaceutically acceptable salt, a polymorph, or a solvate thereof, and one or more pharmaceutically acceptable carriers.

In a third aspect of the present invention, provided is a kit comprising the etomidate derivative of the present invention, or a pharmaceutically acceptable salt, a polymorph, or a solvate thereof, or the pharmaceutical composition of the present invention.

In a fourth aspect of the present invention, provided is the etomidate derivative of the present invention, or a pharmaceutically acceptable salt, a polymorph, or a solvate thereof, for use in anesthesia.

In a fifth aspect of the present invention, provided is use of the etomidate derivative of the present invention, or a pharmaceutically acceptable salt, a polymorph, or a solvate thereof in the manufacture of an anesthetic medicament.

In a sixth aspect of the present invention, provided is an anesthetic method, comprising administration of an effective amount of the etomidate derivative of the present invention, or a pharmaceutically acceptable salt, a polymorph, or a solvate thereof.

In a seventh aspect of the present invention, provided is a method for preparing the etomidate derivative of the present invention, including:

preparing the etomidate derivative from a compound of Formula 2:

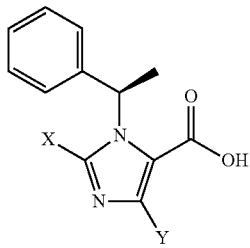

Formula 2 wherein,

X and Y are independently halogen or hydrogen, with the proviso that X and Y are not hydrogen at the same time.

In an eighth aspect of the present invention, provided is an intermediate for the preparation of the etomidate derivative of the present invention, or a salt, a polymorph, or a solvate thereof. The intermediate has the structure of Formula 2:

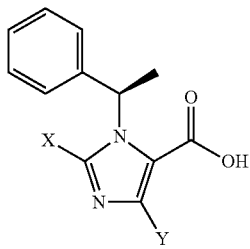

Formula 2 wherein,

X and Y are independently halogen or hydrogen, with the proviso that X and Y are not hydrogen at the same time.

In a ninth aspect of the present invention, provided is use of the compound of Formula 2, or a salt, a polymorph, or a solvate thereof in the preparation of the etomidate derivative of the present invention.

In a tenth aspect of the present invention, provided is another method for preparing the etomidate derivative of the present invention, including:

preparing the etomidate derivative from a compound of Formula 3:

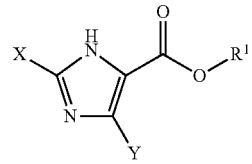

Formula 3 wherein,

X and Y are independently halogen or hydrogen, with the proviso that X and Y are not hydrogen at the same time; and $R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl.

In an eleventh aspect of the present invention, provided is another intermediate for the preparation of the etomidate derivative of the present invention, or a salt, a polymorph, or a solvate thereof. The intermediate has the structure of Formula 3:

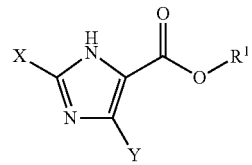

Formula 3 wherein,

X and Y are independently halogen or hydrogen, with the proviso that X and Y are not hydrogen at the same time; and $R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl.

In a twelfth aspect of the present invention, provided is use of the compound of Formula 3, or a salt, a polymorph, or a solvate thereof in the preparation of the etomidate derivative of the present invention.

DETAILED DESCRIPTION OF THE INVENTION

Definitions

Unless otherwise defined below, all technical and scientific terms used herein are intended to have the same meanings as those commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are put forth to better illustrate the present invention.

The term "include", "comprise", "have", "contain" or "involve", as well as other variations used herein are inclusive or open-ended, and do not exclude additional, unrecited elements or method steps.

The term "substituted" as used herein means that one or more (e.g., 1, 2, 3 or 4) hydrogen atoms on the designated atom are replaced with specified groups, provided that the designated atom's normal valency under the existing circumstances is not exceeded, and that the substitution results in a stable compound. Combinations of substituents and/or variables are permissible only if such combinations result in stable compounds.

The term "optionally substituted" as used herein means that the structure described therein can be unsubstituted or substituted with a specified group, radical or moiety.

The term "halogen" as used herein refers to fluorine, chlorine, bromine, or iodine, preferably fluorine, chlorine or bromine.

The term "$C_{1-6}$ alkyl" as used herein refers to a saturated, linear or branched hydrocarbon group having 1-6 carbon atoms, such as methyl, ethyl, propyl, isopropyl, n-butyl, isobutyl, sec-butyl, tent-butyl, n-pentyl, isopentyl, neo-pentyl, n-hexyl, isohexyl and the like, preferably methyl, ethyl, propyl, isopropyl, n-butyl or isobutyl.

The term "$C_{2-6}$ alkenyl" as used herein refers to an unsaturated, linear or branched hydrocarbon group having at least one carbon-carbon double bond and 2-6 carbon atoms, such as ethenyl, 1-propenyl, 2-propenyl (allyl), isopropenyl, 2-methyl-1-propenyl, 1-butenyl, 2-butenyl and the like.

The term "$C_{2-6}$ alkynyl" as used herein refers to an unsaturated, linear or branched hydrocarbon group having at least one carbon-carbon triple bond and 2-6 carbon atoms, such as ethynyl, 1-propynyl, 2-propynyl, 1-butynyl, 2-butynyl and the like.

The term "$C_{3-6}$ cycloalkyl" as used herein refers to a saturated monocyclic hydrocarbon group having 3-6 carbon atoms, such as cyclopropyl, cyclobutyl, cyclopentyl, cyclohexyl and the like.

The term "$C_{6-10}$ aryl" as used herein refers to an aromatic group having 6-10 carbon atoms, such as phenyl or naphthyl.

The term "$C_{1-6}$ alkoxyl" as used herein refers to a saturated monovalent hydrocarbon group of the formula —O—$C_{1-6}$ alkyl, wherein the term "$C_{1-6}$ alkyl" is defined as above, e.g., methoxy, ethoxy, n-propoxy, isopropoxy, n-butoxy, isobutoxy, tert-butoxy, sec-butoxy, pentyloxy, isopentyloxy, n-hexyloxy and the like.

The term "$C_{2-7}$ alkoxycarbonyl" as used herein refers to a $C_{1-6}$ alkoxyl attached to the rest of the molecule through a carbonyl bond, wherein the term "$C_{1-6}$ alkoxyl" is defined as above, e.g., methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, pentyloxycarbonyl, isopentyloxycarbonyl, n-hexyloxycarbonyl and the like.

The term "salt" as used herein refers to a salt formed from an acid and the nitrogen atom on the imidazole ring, wherein the acid refers to an inorganic acid or an organic acid commonly used in the field of organic chemistry that can react with the nitrogen atom on the imidazole ring to form a salt. Examples of the inorganic acid include, but are not limited to, hydrochloric acid, hydrobromic acid, hydroiodic acid, sulfuric acid, pyrosulfuric acid, phosphoric acid, nitric acid, etc. Examples of the organic acid include, but are not limited to, formic acid, acetic acid, propionic acid, butyric acid, pivalic acid, trifluoroacetic acid, difluoroacetic acid, fluoroacetic acid, acetoacetic acid, benzoic acid, methanesulfonic acid, ethanesulfonic acid, trifluoromethanesulfonic acid, benzenesulfonic acid, p-toluenesulfonic acid, naphthalenesulfonic acid, camphorsulfonic acid, etc.

The term "pharmaceutically acceptable salt" as used herein refers to a salt formed from a pharmaceutically acceptable acid and the nitrogen atom on the imidazole ring. Examples of the pharmaceutically acceptable acid include, but are not limited to, hydrochloric acid, hydrobromic acid, sulfuric acid, phosphoric acid, acetic acid, propionic acid, methanesulfonic acid, ethanesulfonic acid, benzenesulfonic acid, p-toluenesulfonic acid, naphthalenesulfonic acid, camphorsulfonic acid, etc.

The compound of the present invention may exist in the form of crystal or polymorph, and may be in the form of a single polymorph or a mixture of more than one polymorph in any ratio.

The compound of the present invention may exist in the form of a solvate, especially a hydrate, wherein the compound of the present invention contains a polar solvent, in particular water, ethanol, isopropanol, ethyl acetate or acetone, for example, as a structural element of the crystal lattice of the compound. Polar solvents, in particular water, may exist in a stoichiometric or non-stoichiometric amount.

Compounds

It is one object of the present invention to provide an etomidate derivative, or a pharmaceutically acceptable salt, a polymorph, or a solvate thereof. The etomidate derivative of the present invention not only has good anesthetic activity, rapid onset, and short duration of action, but also shows little inhibition to the secretion of cortisol and/or corticosterone in animal, and therefore has both favorable anesthetic effect and safety profiles.

Specifically, the present invention provides an etomidate derivative of Formula 1 as below:

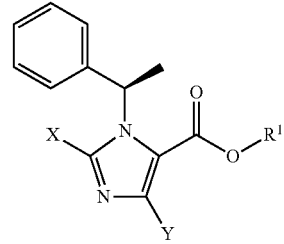

Formula 1 wherein,

X and Y are independently halogen or hydrogen, with the proviso that X and Y are not hydrogen at the same time; and $R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl, or a pharmaceutically acceptable salt, a polymorph, or a solvate thereof According to an embodiment of the present invention, one of X and Y is halogen, and the other is hydrogen.

According to another embodiment of the present invention, X and Y are independently halogen.

According to an embodiment of the present invention, X and Y are the same halogen.

According to another embodiment of the present invention, X and Y are different halogens.

According to an embodiment of the present invention, X and Y are independently fluorine, chlorine, bromine, or hydrogen, with the proviso that X and Y are not hydrogen at the same time.

According to an embodiment of the present invention, $R^1$ is $C_{1-6}$ alkyl, e.g., methyl, ethyl, propyl, isopropyl, n-butyl or isobutyl.

According to an embodiment of the present invention, the etomidate derivative of the present invention is selected from the group consisting of:

Compound 1

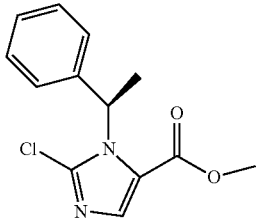

Compound 2

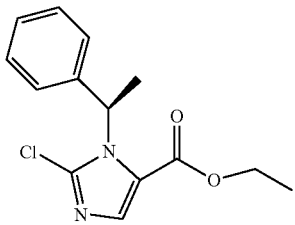

Compound 3

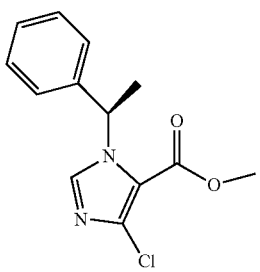

Compound 4

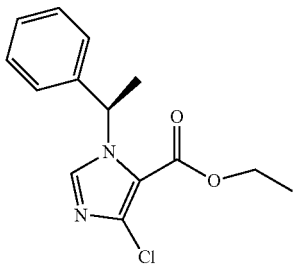

Compound 5

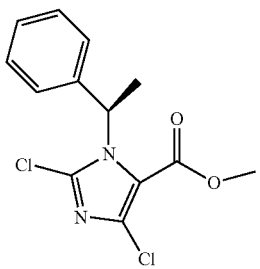

Compound 6

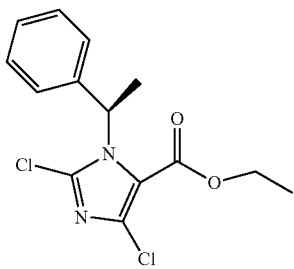

Compound 7

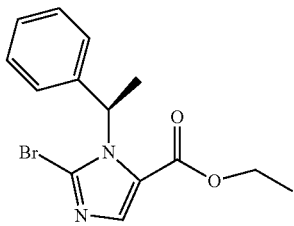

Compound 8

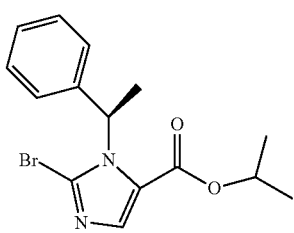

Compound 9

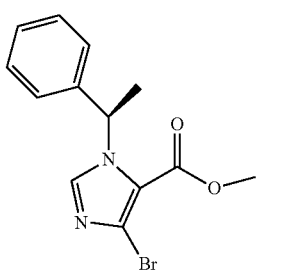

Compound 10

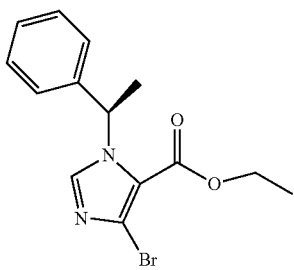

Compound 11

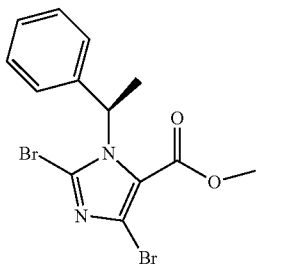

Compound 12
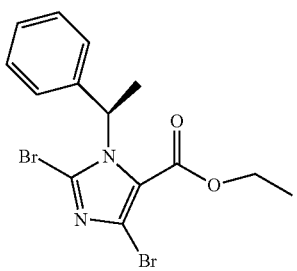
Compound 13
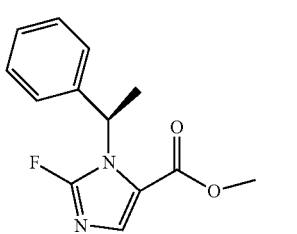
Compound 14
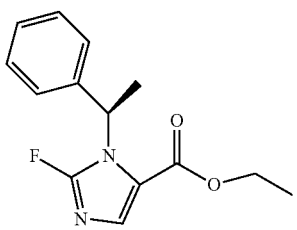
Compound 15
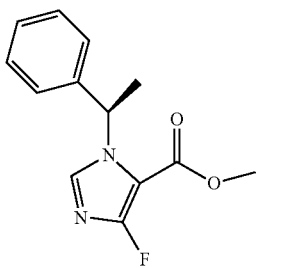
Compound 16
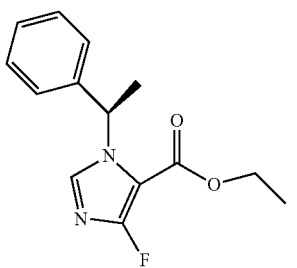
Compound 17
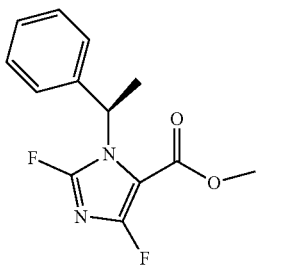
Compound 18
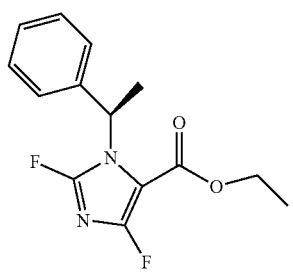
Compound 19
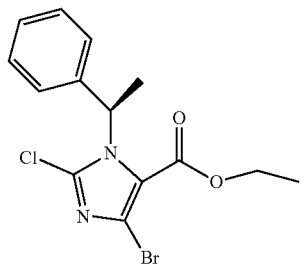
Compound 20
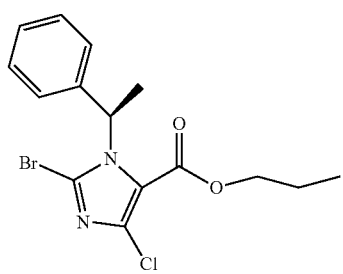
Compound 21
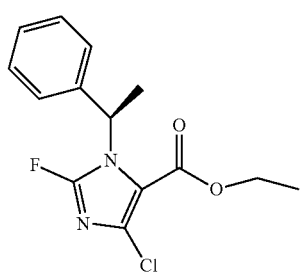
Compound 22
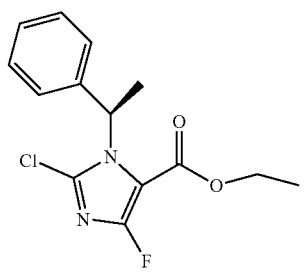
Compound 23
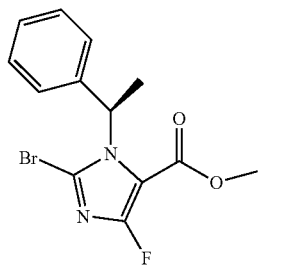

-continued

Compound 24

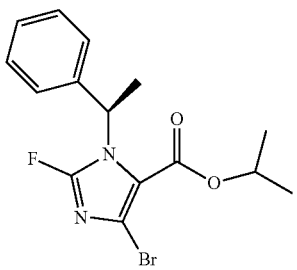

Compound 25

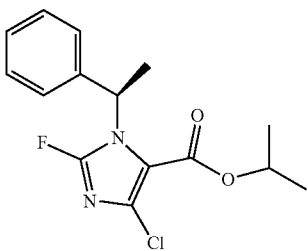

Compound 26

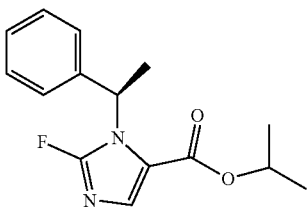

Compound 27

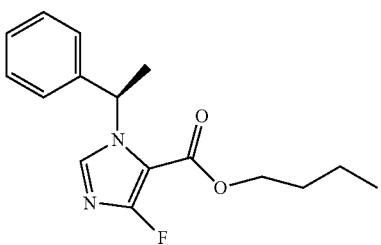

Compound 28

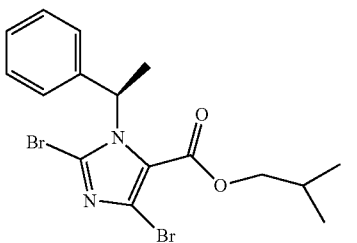

Compound 29

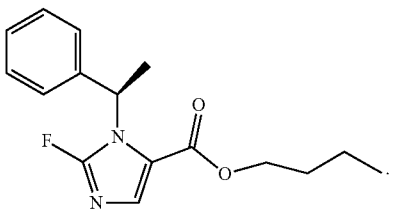

Pharmaceutical Composition and Kit

It is another object of the present invention to provide a pharmaceutical composition comprising the etomidate derivative of the present invention, or a pharmaceutically acceptable salt, a polymorph, or a solvate thereof, and one or more pharmaceutically acceptable carriers.

The term "pharmaceutically acceptable carrier" used in the present invention refers to a diluent, adjuvant, excipient, or vehicle administered together with the therapeutic agent, which, according to sound medical judgment, is suitable for contacting the tissues of human and/or other animals without undue toxicity, irritation, allergic reaction or other problems or complications beyond a reasonable benefit/risk ratio.

The pharmaceutically acceptable carrier which can be employed in the pharmaceutical composition of the present invention may includes, but is not limited to, sterile liquids, such as water and oils, including oils of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The composition, if desired, can also contain minor amounts of wetting agents, emulsifying agents, or pH buffering agents.

The pharmaceutical composition of the present invention may be administered via suitable routes. Preferably, the pharmaceutical composition of the present invention is administered via a parenteral route, e.g., via an intravenous, intraarterial, subcutaneous, intraperitoneal, intramuscular or percutaneous route. More preferably, the pharmaceutical composition of the present invention is administered via an intravenous route.

It is another object of the present invention to provide a kit comprising the etomidate derivative of the present invention, or a pharmaceutically acceptable salt, a polymorph, or a solvate thereof, or the pharmaceutical composition of the present invention.

Treatment Method and Use

It is another object of the present invention to provide the etomidate derivative of the present invention, or a pharmaceutically acceptable salt, a polymorph, or a solvate thereof, for use in anesthesia, particularly intravenous anesthesia.

It is another object of the present invention to provide use of the etomidate derivative of the present invention, or pharmaceutically acceptable salt, a polymorph, or a solvate thereof in the manufacture of an anesthetic medicament. Preferably, the medicament is administered via a parenteral route, e.g., via an intravenous, intraarterial, subcutaneous, intraperitoneal, intramuscular or percutaneous route. More preferably, the medicament is administered via an intravenous route.

It is another object of the present invention to provide an anesthetic method, comprising administration of an effective amount of the etomidate derivative of the present invention, or a pharmaceutically acceptable salt, a polymorph, or a solvate thereof. Preferably, the administration is performed via a parenteral route, e.g., via an intravenous, intraarterial, subcutaneous, intraperitoneal, intramuscular or percutaneous route. More preferably, the administration is performed via an intravenous route.

Preparation Method

It is another object of the present invention to provide a method for preparing the etomidate derivative of the present invention, including:

preparing the etomidate derivative from a compound of Formula 2:

Formula 2

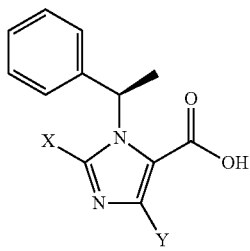

wherein,

X and Y are independently halogen or hydrogen, with the proviso that X and Y are not hydrogen at the same time.

According to an embodiment of the present invention, one of X and Y is halogen, and the other is hydrogen.

According to another embodiment of the present invention, X and Y are independently halogen.

According to an embodiment of the present invention, X and Y are the same halogen.

According to another embodiment of the present invention, X and Y are different halogens.

According to an embodiment of the present invention, X and Y are independently fluorine, chlorine, bromine, or hydrogen, with the proviso that X and Y are not hydrogen at the same time.

According to an embodiment of the present invention, the compound of Formula 2 is selected from the group consisting of:

Compound 30

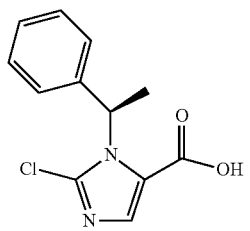

Compound 31

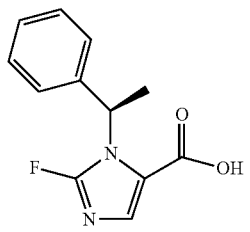

Compound 32

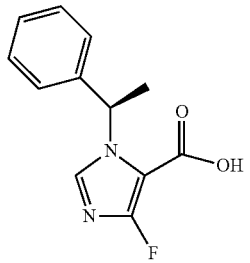

Compound 33

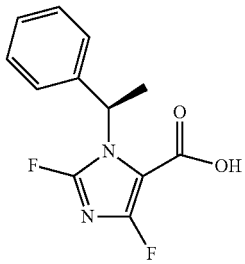

Compound 34

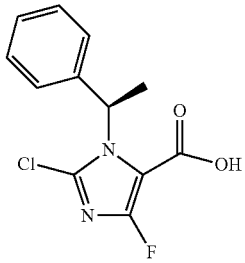

Compound 35

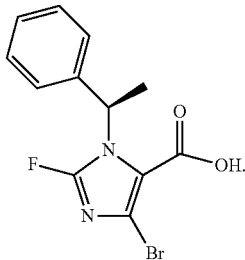

According to an embodiment of the present invention, the etomidate derivative of Formula 1 can be prepared according to the following Scheme A (condensation with an ester) from the compound of Formula 2:

Scheme A

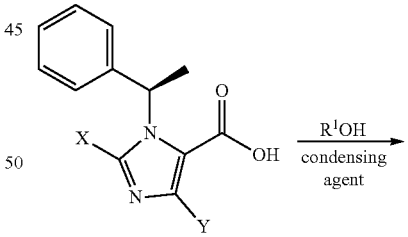

Formula 2

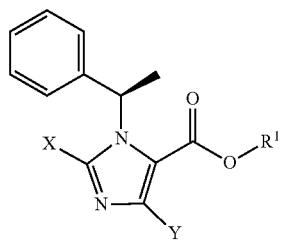

Formula 1 wherein X and Y and $R^1$ are defined as above.

According to an embodiment of the present invention, the condensing agent is a compound comprising a carbodiimide structure, e.g., EDCI or DCC, etc.

Preferably, the reaction described above is performed at a temperature of 10° C. to 50° C.

Preferably, the molar ratio of the compound of Formula 2 to $R^1OH$ to the condensing agent is 1:(1-10):(1-15).

According to another embodiment of the present invention, the etomidate derivative of Formula 1 can be prepared according to the following Scheme B from the compound of Formula 2:

Scheme B

Formula 2

Formula 1 wherein X, Y and $R^1$ are defined as above.

According to an embodiment of the present invention, the halogenating agent is thionyl chloride, oxalyl chloride or a similar chemical reagent.

According to an embodiment of the present invention, the alkaline reagent is nitrogen-containing organic reagent, e.g., triethylamine, DMAP, etc.

Preferably, the reaction described above is performed at a temperature of −20° C. to 50° C.

Preferably, the molar ratio of the compound of Formula 2 to $R^1OH$ is 1:(1-10).

According to another embodiment of the present invention, the etomidate derivative of Formula 1 can be prepared according to the following Scheme C from the compound of Formula 2:

Scheme C

Formula 2

Formula 1 wherein X, Y and $R^1$ are defined as above.

According to an embodiment of the present invention, $H^+$ means sulfuric acid, HCl, HBr, etc.

Preferably, the reaction described above is performed at a temperature of −10° C. to 60° C.

Preferably, the molar ratio of the compound of Formula 2 to $R^1OH$ is 1:(5-20).

According to another embodiment of the present invention, the etomidate derivative of Formula 1 can be prepared according to the following Scheme D from the compound of Formula 2:

Scheme D

Formula 2

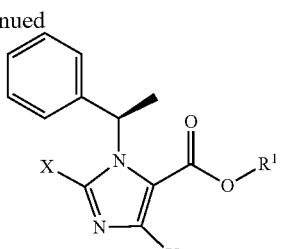

Formula 1 wherein X, Y and $R^1$ are defined as above.

The activating agent is an agent which can activate the acyl group so as to facilitate esterification, e.g., ethyl chloroformate, benzyl chloroformate, etc.

Preferably, the reaction described above is performed at a temperature of −20° C. to 50° C.

Preferably, the molar ratio of the compound of Formula 2 to $R^1OH$ is 1:(1-10).

It is another object of the present invention to provide another method for preparing the etomidate derivative of the present invention, including:

preparing the etomidate derivative from a compound of Formula 3:

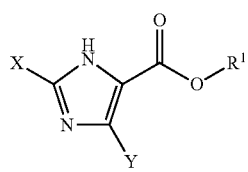

Formula 3 wherein,

X and Y are independently halogen or hydrogen, with the proviso that X and Y are not hydrogen at the same time; and $R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl.

According to an embodiment of the present invention, one of X and Y is halogen, and the other is hydrogen.

According to another embodiment of the present invention, X and Y are independently halogen.

According to an embodiment of the present invention, X and Y are the same halogen.

According to an embodiment of the present invention, X and Y are different halogens.

According to an embodiment of the present invention, X and Y are independently fluorine, chlorine, bromine, or hydrogen, with the proviso that X and Y are not hydrogen at the same time.

According to an embodiment of the present invention, $R^1$ is $C_{1-6}$ alkyl, e.g., methyl, ethyl, propyl, isopropyl, n-butyl or isobutyl.

According to an embodiment of the present invention, the compound of Formula 3 is selected from the group consisting of:

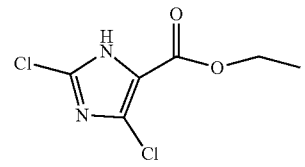

Compound 36

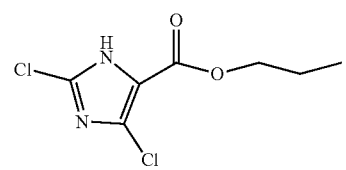

Compound 37

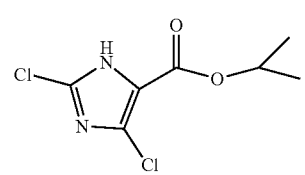

Compound 38

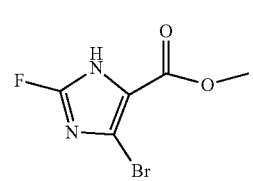

Compound 39

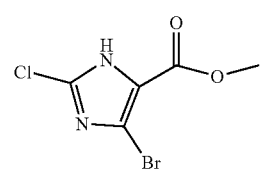

Compound 40

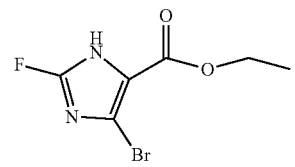

Compound 41

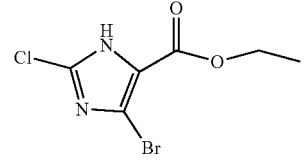

Compound 42

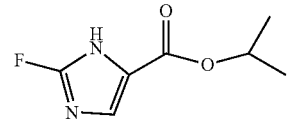

Compound 43

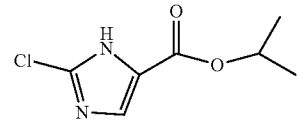

Compound 44

-continued

Compound 45

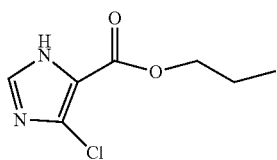

Compound 46

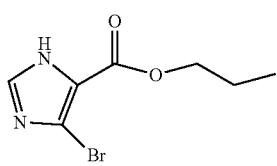

Compound 47

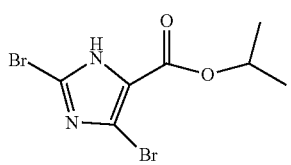

Compound 48

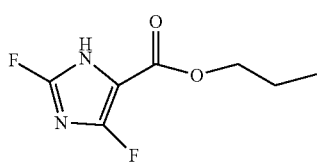

Compound 49

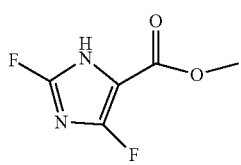

Compound 50

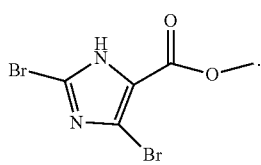

According to an embodiment of the present invention, the etomidate derivative of Formula 1 can be prepared according to the following Scheme E from the compound of Formula 2:

Scheme E

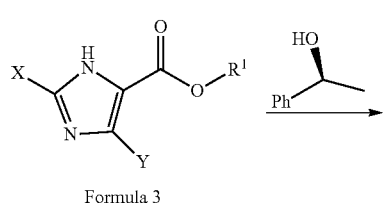

Formula 3

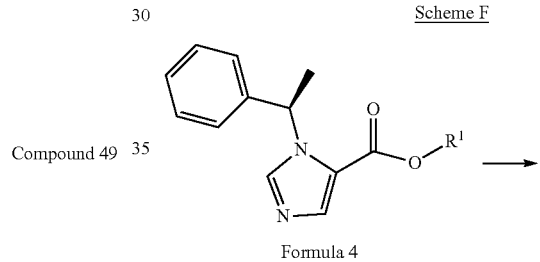

Formula 1 wherein X, Y and $R^1$ are defined as above.

According to an embodiment of the present invention, the reaction in Scheme E is performed in the presence of $Ph_3P$ and DEAD.

Preferably, the reaction described above is performed at a temperature of −20° C. to 60° C.

Preferably, the molar ratio of the compound of Formula 3 to S-phenethanol is 1:(1-10).

It is another object of the present invention to provide other methods for preparing the etomidate derivative of the present invention. For example, the etomidate derivative of Formula 1 can be prepared according to the following Schemes F and G from compounds of Formulae 4 and 5, respectively:

Scheme F

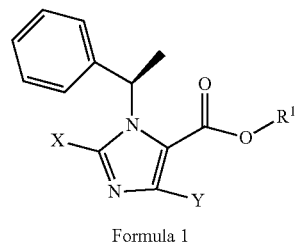

Formula 4

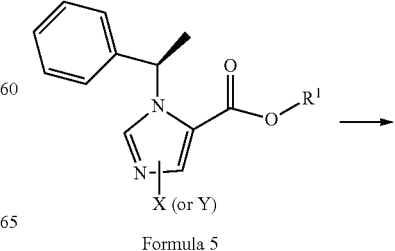

Formula 1

For example, when X and Y are simultaneously chlorine or bromine, the compound of Formula 1 can be prepared by reacting the compound of Formula 4 with NCS or NBS.

Scheme G

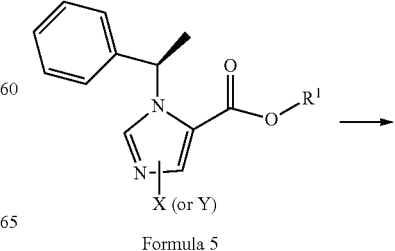

Formula 5

-continued

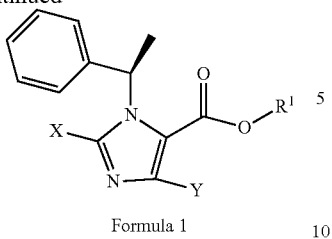

Formula 1

For example, when one of X and Y is fluorine or chlorine, and the other is bromine, the compound of Formula 1 can be prepared by reacting the compound of Formula 5 with NCS or NBS.

Intermediate Compounds

It is another object of the present invention to provide an intermediate compound for the preparation of the etomidate derivative of the present invention, wherein the intermediate compound has the structure of Formula 2:

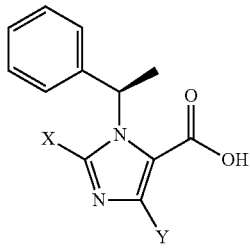

Formula 2 wherein,

X and Y are independently halogen or hydrogen, with the proviso that X and Y are not hydrogen at the same time.

According to an embodiment of the present invention, one of X and Y is halogen, and the other is hydrogen.

According to another embodiment of the present invention, X and Y are independently halogen.

According to an embodiment of the present invention, X and Y are the same halogen.

According to another embodiment of the present invention, X and Y are different halogens.

According to an embodiment of the present invention, X and Y are independently fluorine, chlorine, bromine, or hydrogen, with the proviso that X and Y are not hydrogen at the same time.

According to an embodiment of the present invention, the compound of Formula 2 is selected from the group consisting of:

Compound 30

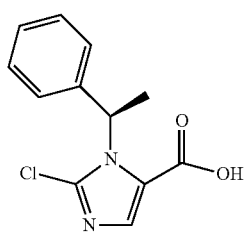

Compound 31

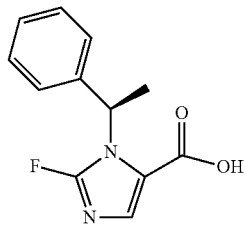

Compound 32

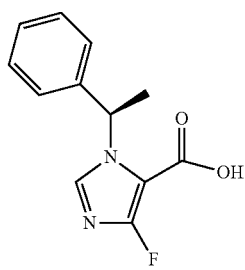

Compound 33

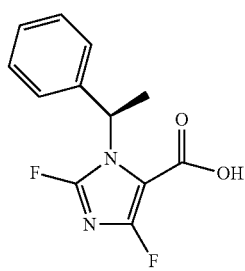

Compound 34

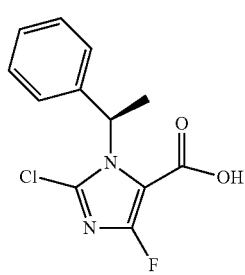

Compound 35

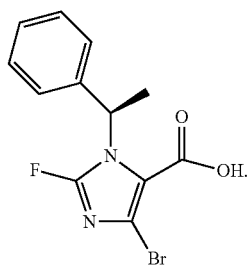

The compound of Formula 2 can be obtained through hydrolysis of the etomidate derivative of Formula 1. Thus, the compound of Formula 2 can also be used as an impurity reference substance for the compound of Formula 1.

Scheme H

Formula 1 (structure with hydrolysis arrow)

Formula 2 (structure)

It is another object of the present invention to provide another intermediate compound for the preparation of the etomidate derivative of the present invention, wherein the intermediate compound has the structure of Formula 3:

Formula 3 (structure)

wherein,

X and Y are independently halogen or hydrogen, with the proviso that X and Y are not hydrogen at the same time; and $R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl.

According to an embodiment of the present invention, one of X and Y is halogen, and the other is hydrogen.

According to another embodiment of the present invention, X and Y are independently halogen.

According to an embodiment of the present invention, X and Y are the same halogen.

According to another embodiment of the present invention, X and Y are different halogens.

According to an embodiment of the present invention, X and Y are independently fluorine, chlorine, bromine, or hydrogen, with the proviso that X and Y are not hydrogen at the same time.

According to an embodiment of the present invention, $R^1$ is $C_{1-6}$ alkyl, e.g., methyl, ethyl, propyl, isopropyl, n-butyl or isobutyl.

According to an embodiment of the present invention, the compound of Formula 3 is selected from the group consisting of:

Compound 36

Compound 37

Compound 38

Compound 39

Compound 40

Compound 41

Compound 42

Compound 43

Compound 44

-continued

Compound 45

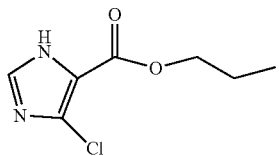

Compound 46

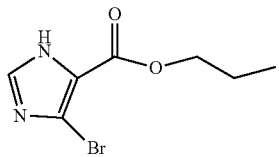

Compound 47

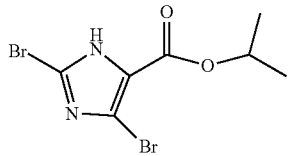

Compound 48

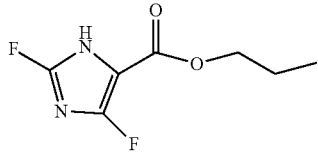

Compound 49

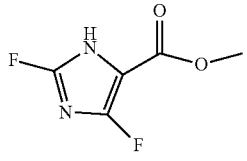

Compound 50

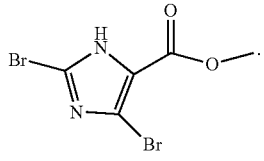

The compound of Formula 3 can be prepared according to conventional methods from commercially available raw materials, for example, by referring to the methods described in the following literatures: [1] Journal of Organic Chemistry, 2001 (20), 76, 8477-8482; [2] Journal of Medicine Chemistry, 2008 (7), 51, 2244-2253; [3] Journal of American Chemical Society, 1973, 95, 4619; and [4] Journal of Organic Chemistry, 1984 (11), 49, 1951-1954.

EXAMPLES

The present invention has been further described in detail with reference to the following examples for apparency of the purpose and technical solution of the present invention. It should be understood that these examples are provided merely for further illustration of the present invention, but should not be construed as limitation to the scope of the present invention. Any non-essential modifications and/or adjustments to the technical solutions of the present invention by a person skilled in the art based on the above disclosure of the present invention all fall within the protection scope of the present invention. In addition, the specific experimental procedures not mentioned in the examples below are carried out according to conventional experimental procedures.

The abbreviations as used herein have the following meanings:

| | |
|---|---|
| NCS | N-chlorosuccinimide |
| NBS | N-bromosuccinimide |
| Ph$_3$P | triphenylphosphine |
| DEAD | diethyl azodicarboxylate |
| NaNO$_2$ | sodium nitrite |
| THF | tetrahydrofuran |
| EDCI | 1-ethyl-3-(3-dimethylaminopropyl)carbodiimide hydrochloride |
| DCC | dicyclohexylcarbodiimide |
| DMF | N,N-dimethylformamide |
| DMAP | 4-N,N-dimethylaminopyridine |
| HBF$_4$ | fluoroboric acid |
| ACTH$_{1-24}$ | Adrenocorticotropic hormone amino-terminal bioactive peptide |

Preparation of the Compound of Formula 3

Example 1

Preparation of ethyl 1H-4-chloroimidazole-5-carboxylate

At room temperature, commercially available 1H-4-chloroimidazole-5-carboxylic acid (300 mg) was added to ethanol (5 ml), then thionyl chloride (0.5 ml) was added, and the mixture was allowed to react under reflux for 1 hour. The solvent was removed by evaporation under reduced pressure to give ethyl 1H-4-chloroimidazole-5-carboxylate hydrochloride as a white solid. A saturated aqueous NaHCO$_3$ solution was added to neutralize in an ice water bath, and the resulting mixture was extracted with ethyl acetate. The solvent was removed by evaporation under reduced pressure to give the title compound (290 mg).

MS-ESI [M+H]$^+$=175.53

Example 2

Preparation of methyl 1H-4-fluoroimidazole-5-carboxylate

In an ice bath, methyl 1H-imidazole-4-amino-5-carboxylate (0.5 g) was dissolved in 50% HBF$_4$ solution (12.5 ml), and then an aqueous solution (1 ml) of NaNO$_2$ (0.28 g) was added. The mixture was allowed to react continuously under the irradiation of a mercury lamp (234 nm) until no more nitrogen gas evolution occurs. After the reaction is completed, a 1 N ice water solution of NaOH was added to the mixture in an ice bath to adjust the pH to 6. The water layer was extracted with ethyl acetate (20 ml*3). The organic layers were combined, washed with saturated brine, dried over anhydrous sodium sulfate, filtered, and concentrated under reduced pressure. The residue was separated by column chromatography (EA:PE=1:1) to give the title compound (0.23 g) as a colorless oil.

MS-ESI [M+H]$^+$=145.08

Compounds 36-50 were prepared according to the method described in Example 1 or 2, using corresponding commercially available raw materials. The mass spectral data of compound 36-50 are listed in the table below:

| Compound No. | MS-ESI [M + H]$^+$ |
|---|---|
| 36 | 210.01 |
| 37 | 224.02 |

-continued

| Compound No. | MS-ESI [M + H]+ |
|---|---|
| 38 | 224.03 |
| 39 | 223.97 |
| 40 | 240.41 |
| 41 | 238.01 |
| 42 | 254.43 |
| 43 | 173.14 |
| 44 | 189.59 |
| 45 | 189.57 |
| 46 | 234.04 |
| 47 | 312.94 |
| 48 | 191.13 |
| 49 | 163.07 |
| 50 | 284.88 |

Preparation of the Compound of Formula 2

Example 3

Preparation of R-1-(1-phenethyl)-1H-4-fluoroimidazole-5-carboxylic acid (Compound 32)

Methyl R-1-(1-phenethyl)-1H-4-fluoroimidazole-5-carboxylate (2.48 g, 10 mmol) was dissolved in methanol (30 ml) while stirring in an ice bath, and then 1 N NaOH solution was added dropwise. The reaction was monitored by TLC. After the reaction is completed, methanol was removed by evaporation under reduced pressure. The water layer was adjusted to pH 5 using 1 N HCl, and then extracted with ethyl acetate (25 ml*3). The organic layers were combined, washed with saturated brine, dried over anhydrous sodium sulfate, filtered and concentrated to give the title compound (2.22 g, yield 94.8%) as a white solid.

MS-ESI [M+H]+=235.18

Compounds 30-31 and 33-35 were prepared according to the method described in Example 3, using corresponding raw materials. The mass spectral data of compounds 30-31 and 33-35 are listed in the table below:

| Compound No. | MS-ESI [M + H]+ |
|---|---|
| 30 | 251.65 |
| 31 | 235.19 |
| 33 | 253.21 |
| 34 | 269.64 |
| 35 | 314.09 |

Preparation of the Etomidate Derivative of Formula 1

Example 4

Preparation of methyl R-1-(1-phenethyl)-1H-2-fluoroimidazole-5-carboxylate (Compound 13)

To a mixture of methyl 1H-2-fluoroimidazole-5-carboxylate (144 mg) and Ph$_3$P (325 mg) in THF (3 ml) was added S-phenethanol (122 mg) in THF (2 ml) dropwise at −30° C. Then DEAD (220 mg) in THF (2 ml) was added dropwise to the reaction solution. After addition, the reaction solution was then warmed to 0° C. The reaction was monitored by TLC. After the reaction is completed, the solvent was removed by evaporation under reduced pressure. The residue was separated by column chromatography (EA:PE=1:3) to give the title compound (73 mg) as a colorless oil.

MS-ESI [M+H]+=249.21

Example 5

Preparation of ethyl R-1-(1-phenethyl)-1H-2-fluoroimidazole-5-carboxylate (Compound 14)

The title compound was prepared according to the method described in Example 4, using ethyl 1H-2-fluoroimidazole-5-carboxylate as the raw material.

MS-ESI [M+H]+=263.24

Example 6

Preparation of ethyl R-1-(1-phenethyl)-1H-2,4-difluoroimidazole-5-carboxylate (Compound 18)

The title compound was prepared according to the method described in Example 4, using ethyl 1H-2,4-difluoroimidazole-5-carboxylate as the raw material.

MS-ESI [M+H]+=281.23

Example 7

Preparation of ethyl R-1-(1-phenethyl)-1H-4-chloroimidazole-5-carboxylate (Compound 4)

1) Ethyl 1H-4-chloroimidazole-5-carboxylate: At room temperature, 1H-4-chloroimidazole-5-carboxylic acid (300 mg) was added to ethanol (5 ml) while stirring, and then thionyl chloride (0.5 ml) was added. The mixture was allowed to react under reflux for 1 hour. The solvent was removed by evaporation under reduced pressure to give ethyl 1H-4-chloroimidazole-5-carboxylate hydrochloride as a white solid. An ice water solution of sodium bicarbonate was slowly added to neutralize in an ice water bath, and the resulting mixture was extracted with ethyl acetate. The solvent was removed by evaporation under reduced pressure to give ethyl 1H-4-chloroimidazole-5-carboxylate (280 mg).

2) The title compound was prepared according to the method described in Example 4, using ethyl 1H-4-chloroimidazole-5-carboxylate as the raw material.

MS-ESI [M+H]+=279.69

Example 8

Preparation of methyl R-1-(1-phenethyl)-1H-4-fluoroimidazole-5-carboxylate (Compound 15)

1) Methyl 1H-imidazole-4-fluoro-5-carboxylate: In an ice bath, methyl 1H-imidazole-4-amino-5-carboxylate (0.5 g) was dissolved in 50% HBF$_4$ solution (12.5 ml) in an ice bath, and then an aqueous solution (1 ml) of NaNO$_2$ (0.28 g) was added. The mixture was allowed to react continuously under the irradiation of a mercury lamp (234 nm) until no more nitrogen gas evolution occurs. After the reaction is completed, a 1 N ice water solution of NaOH was added to the mixture in an ice bath to adjust the pH to above 6. The water layer was extracted with ethyl acetate (20 ml*3). The organic layers were combined, washed with saturated brine, dried over anhydrous sodium sulfate, filtered, and concentrated under reduced pressure. The residue was separated by column chromatography (EA:PE=1:1) to give methyl 1H-4-fluoroimidazole-5-carboxylate (0.23 g) as a colorless oil.

2) The title compound was prepared according to the method described in Example 4, using methyl 1H-4-fluoroimidazole-5-carboxylate as the raw material.

MS-ESI [M+H]+=249.22

¹H-NMR (DMSO, 400 MHz): 1.73-1.84 (t, 3H); 3.68 (s, 3H); 6.13 (q, 1H), 7.1-7.3 (m, 5H).
F-NMR δ: −113.40 (s).

Example 9

Preparation of ethyl R-1-(1-phenethyl)-1H-4-fluoroimidazole-5-carboxylate (Compound 16)

To a mixture of ethyl 1H-4-fluoroimidazole-5-carboxylate (158 mg, 1.1 mmol) and Ph$_3$P (340 mg, 1.3 mmol) in dry THF (3 ml) was added S-phenethanol (134 mg, 1.1 mmol) in dry THF (2 ml) dropwise. Then DEAD (230 mg, 1.32 mmol) in dry THF (2 ml) was added dropwise to the reaction solution. After addition, the reaction solution was then slowly warmed to 0° C. The reaction was monitored by TLC. After the reaction is completed, the solvent was removed by evaporation under reduced pressure. The residue was separated by column chromatography (EA:PE=1:3) to give the title compound (81 mg, yield 28%) as a colorless oil.

MS-ESI [M+H]$^+$=263.24
¹H-NMR (CD$_3$Cl, 400 MHz): 1.31 (t, J=7.1 Hz, 3H); 1.96 (d, J=7.2 Hz, 3H); 4.20-4.33 (q, J=7.1 Hz, 2H); 6.22-6.31 (m, 1H), 7.16-7.38 (m, 5H).
F-NMR δ: −113.40 (s).

Compounds 1-3, 5-12, 17 and 19-29 were prepared according to the method described in Example 4-9, using corresponding compounds of Formula 3 as the raw materials.

Example 10

Preparation of ethyl R-1-(1-phenethyl)-1H-2-chloroimidazole-5-carboxylate (Compound 2), ethyl R-1-(1-phenethyl)-1H-4-chloroimidazole-5-carboxylate (Compound 4) and ethyl R-1-(1-phenethyl)-1H-2,4-dichloroimidazole-5-carboxylate (Compound 6)

Ethyl R-1-(1-phenethyl)-1H-imidazole-5-carboxylate (488 mg, 2 mmol) and NCS (280 mg, 2.1 mmol) were dissolved in acetonitrile (20 ml) at room temperature. The mixture was heated to reflux, and allowed to react for 12 hours. After the reaction is completed, the solvent was removed by evaporation under reduced pressure. The residue was separated by column chromatography to give ethyl R-1-(1-phenethyl)-1H-2-chloroimidazole-5-carboxylate (80 mg), ethyl R-1-(1-phenethyl)-1H-4-chloroimidazole-5-carboxylate (120 mg) and ethyl R-1-(1-phenethyl)-1H-2,4-dichloroimidazole-5-carboxylate (50 mg), respectively.

Ethyl R-1-(1-phenethyl)-1H-2-chloroimidazole-5-carboxylate:
(CH$_3$Cl, 400 MHz) δ: 1.30 (t, J=7.1 Hz, 3H); 2.00 (d, J=7.2 Hz, 3H); 4.22-4.38 (q, J=7.1 Hz, 2H); 6.25-6.38 (m, 1H), 7.15-7.37 (m, 5H); 7.55 (s, 1H).
MS-ESI [M+H]$^+$=279.71.

Ethyl R-1-(1-phenethyl)-1H-4-chloroimidazole-5-carboxylate:
¹H-NMR (CH$_3$Cl, 400 MHz) δ: 1.33 (t, J=7.1 Hz, 3H); 1.97 (d, J=7.2 Hz, 3H); 4.24-4.31 (q, J=7.1 Hz, 2H); 6.65-6.77 (m, 1H); 7.15-7.35 (m, 5H); 7.70 (s, 1H).
MS-ESI [M+H]$^+$=279.70.

Ethyl R-1-(1-phenethyl)-1H-2,4-dichloroimidazole-5-carboxylate:
¹H-NMR (CH$_3$Cl, 400 MHz) δ: 1.31 (t, J=7.1 Hz, 3H); 1.96 (d, J=7.2 Hz, 3H); 4.26-4.36 (q, J=7.1 Hz, 2H); 6.60-6.69 (m, 1H); 7.16-7.36 (m, 5H).
MS-ESI [M+H]$^+$=341.15.

Example 11

Preparation of ethyl R-1-(1-phenethyl)-1H-2-bromoimidazole-5-carboxylate (Compound 7), ethyl R-1-(1-phenethyl)-1H-4-bromoimidazole-5-carboxylate (Compound 10) and ethyl R-1-(1-phenethyl)-1-hydrogen-2,4-dibromoimidazole-5-carboxylate (Compound 12)

The title compounds were prepared according to the method described in Example 10, using ethyl R-1-(1-phenethyl)-1H-imidazole-5-carboxylate as the raw material and NBS as the brominating agent.

Ethyl R-1-(1-phenethyl)-1H-2-bromoimidazole-5-carboxylate:
¹H-NMR (CH$_3$Cl, 400 MHz) δ: 1.30 (t, J=7.1 Hz, 3H); 2.00 (d, J=7.2 Hz, 3H); 4.22-4.38 (q, J=7.1 Hz, 2H); 6.26-6.40 (m, 1H), 7.09-7.39 (m, 5H); 7.58 (s, 1H).
MS-ESI [M+H]$^+$=324.17.

Ethyl R-1-(1-phenethyl)-1H-4-bromoimidazole-5-carboxylate:
¹H-NMR (CH$_3$Cl, 400 MHz) δ: 1.30 (t, J=7.1 Hz, 3H); 2.00 (d, J=7.2 Hz, 3H); 4.20-4.27 (q, J=7.1 Hz, 2H); 6.65-6.71 (m, 1H), 7.36-7.12 (m, 5H); 7.75 (s, 1H).
MS-ESI [M+H]$^+$=324.18.

Ethyl R-1-(1-phenethyl)-1H-2,4-dibromoimidazole-5-carboxylate:
¹H-NMR (CH$_3$Cl, 400 MHz) δ: 1.31 (t, J=7.1 Hz, 3H); 1.99 (d, J=7.1 Hz, 3H); 4.35-4.16 (q, J=7.1 Hz, 2H); 6.49-6.6 (m, 1H); 7.42-7.09 (m, 5H).
MS-ESI [M+H]$^+$=403.07.

Example 12

Preparation of ethyl R-1-(1-phenethyl)-1H-2-chloro-4-bromo-imidazole-5-carboxylate (Compound 19)

The title compound was prepared according to the method described in Example 10, using ethyl R-1-(1-phenethyl)-1H-2-chloroimidazole-5-carboxylate as the raw material and NBS as the brominating agent.

MS-ESI [M+H]$^+$=358.61.

Example 13

Preparation of isopropyl R-1-(1-phenethyl)-1H-2-fluoro-4-chloro-imidazole-5-carboxylate (Compound 24)

The title compound was prepared according to the method described in Example 10, using isopropyl R-1-(1-phenethyl)-1H-2-fluoroimidazole-5-carboxylate as the raw material and NCS as the chlorinating agent.

MS-ESI [M+H]$^+$=356.19.

Example 14

Preparation of isopropyl R-1-(1-phenethyl)-1H-2-fluoro-4-chloro-imidazole-5-carboxylate (Compound 25)

R-1-(1-phenethyl)-1H-2-fluoro-4-chloro-imidazole-5-carboxylic acid (270 mg, 1 mmol) and triethylamine (111 mg, 1.1 mmol) were dissolved in dry dichloromethane (15 ml) at −20° C. Then a solution of ethyl chloroformate (110 mg, 1 mmol) in dry dichloromethane (2 ml) was added dropwise slowly. The reaction mixture was stirred for 1 hour at −20° C., and then filtered. Isopropyl alcohol (0.5 ml) was added dropwise to the filtrate in an ice bath, and the mixture was allowed to react for 4 hours in an ice bath. After the reaction is completed, the reaction solution was washed in sequence with 0.1 N HCl (5 ml*2), saturated NaHCO$_3$ solution (10 ml*2) and saturated brine (15 ml*1). The organic layer was dried over anhydrous sodium sulfate, filtered, and concentrated under reduced pressure. The residue was purified by column chromatography to give the title compound (280 mg, yield 90%) as a colorless oil.

MS-ESI [M+H]$^+$=311.68.

Example 15

Preparation of isopropyl R-1-(1-phenethyl)-1H-2-fluoroimidazole-5-carboxylate (Compound 26)

At room temperature, R-1-(1-phenethyl)-1H-2-fluoroimidazole-5-carboxylic acid (234 mg, 1 mmol), EDCI (250 mg, 1.3 mmol) and DMAP (12 mg, 0.1 mmol) were added to dry dichloromethane (10 ml) while stirring. Then isopropyl alcohol (12 mg, 2 mmol) was added dropwise slowly. The mixture was allowed to react while stirring at room temperature for 6 hours. After the reaction is completed, the reaction solution was washed in sequence with 0.1 N HCl (5 ml*2), saturated NaHCO$_3$ (10 ml*2) and saturated brine (15 ml*1). The organic layer was dried over anhydrous sodium sulfate, filtered, and concentrated under reduced pressure. The residue was purified by column chromatography to give the title compound (248 mg, yield 90%) as a colorless oil.

MS-ESI [M+H]$^+$=277.28.

Example 16

Preparation of n-butyl R-1-(1-phenethyl)-1H-4-fluoroimidazole-5-carboxylate (Compound 27)

The title compound was prepared according to the method described in Example 15, using R-1-(1-phenethyl)-1H-4-fluoroimidazole-5-carboxylic acid and n-butanol as the raw materials.

MS-ESI [M+H]$^+$=291.31.

Example 17

Preparation of isobutyl R-1-(1-phenethyl)-1H-2,4-dibromoimidazole-5-carboxylate (Compound 28)

The title compound was prepared according to the method described in Example 15, using R-1-(1-phenethyl)-1H-2,4-dibromoimidazole-5-carboxylic acid and isobutanol as the raw materials.

MS-ESI [M+H]$^+$=431.09.

Example 18

Preparation of n-butyl R-1-(1-phenethyl)-1H-2-fluoroimidazole-5-carboxylate (Compound 29)

In an ice bath, R-1-(1-phenethyl)-1H-2-fluoroimidazole-5-carboxylic acid (470 mg, 2 mmol) was added to dry dichloromethane (10 ml) while stirring, and then oxalyl chloride (0.5 ml) and a catalytic amount of DMF were added. The ice bath was removed, and the mixture was allowed to react at room temperature for 12 hours. The solvent and excessive oxalyl chloride were removed by evaporation under reduced pressure to give R-1-(1-phenethyl)-1H-2-fluoroimidazole-5-carboxyl chloride.

A solution of R-1-(1-phenethyl)-1H-2-fluoroimidazole-5-carboxyl chloride prepared in the last step in dry dichloromethane (5 ml) was added dropwise slowly to a solution of n-butanol (0.2 ml) and DMAP (300 mg, 2.5 mmol) in dry dichloromethane (10 ml) in an ice bath while stirring. The ice bath was removed, and the mixture was allowed to react at room temperature for 6 hours. After the reaction is completed, the reaction solution was washed in sequence with 0.1 N HCl (5 ml*2), saturated NaHCO$_3$ (10 ml*2) and saturated brine (15 ml*1). The organic layer was dried over anhydrous sodium sulfate, filtered, and concentrated under reduced pressure. The residue was purified by column chromatography to give the title compound (550 mg, yield 95%) as a colorless oil.

MS-ESI [M+H]$^+$=291.30.

Compounds 1-24 were prepared according to the method described in Example 14-18, using corresponding compounds of Formula 2 as the raw materials.

The mass spectral data of compound 1, 3, 5, 8, 9, 11, 17, 20-23 are listed in the table below:

| Compound No. | MS-ESI [M + H]$^+$ |
| --- | --- |
| 1 | 265.68 |
| 3 | 265.70 |
| 5 | 300.13 |
| 8 | 338.18 |
| 9 | 338.19 |
| 11 | 417.08 |
| 17 | 264.22 |
| 20 | 372.64 |
| 21 | 279.69 |
| 22 | 279.71 |
| 23 | 328.13 |

Biological Experimental Examples

Experimental Example 1

Test of ED$_{50}$ and LD$_{50}$ of the etomidate derivative of the present invention in mice Test Drugs and Administration:

Accurately weighed compounds 14, 15, 16 and 18 (5 mg for each of the compounds) were placed in 10 ml centrifuge tubes, respectively. Then 1 ml blank emulsion (20% soybean oil blank emulsion) was added to each tube, and the mixture was sonicated in an ultrasonic apparatus for several minutes to obtain a 5 mg/ml homogeneous emulsion, which was drawn by an injection syringe right before use. An etomidate fat emulsion injection (commercially available, 2 mg/ml) was used as control. The administration concentration in mice was fixed, and the administration volume varied according to actual situation.

Test Method:

ED$_{50}$ and LD$_{50}$ values concerning anesthesia were determined using a sequential method. Administrations in this test were performed on qualified healthy KM mice (male) by by injection at a constant rate via caudal vein for 10 seconds. Before the test, a preliminary trial test was conducted to determine an approximate dosage (administration volume) that leads to anesthetization (or death) in animals, which was then set as the intermediate dosage in the formal test. 2-3 Dosage groups were set above and below the intermediate dosage group with an interval of 0.8. The disappearance of righting reflex or death was used as indicators of pharmacological efficacy or toxicity, respectively. The formal test began with the administration of the intermediate dosage. If animals were anesthetized, a lower dosage was administered; otherwise if animals were not anesthetized, a higher dosage was administered, until the cycle was repeated for 3-4 times. $LD_{50}$ and $ED_{50}$ values of anesthesia were calculated by a sequential method on aot425 software. TI was calculated according to the following equation: $TI=LD_{50}/ED_{50}$.

Test Results:

The test results of $LD_{50}/ED_{50}$ and TI index of the compounds in mice are listed in Table 1:

TABLE 1

Test results of $LD_{50}/ED_{50}$ and TI index of the compounds in mice (n = 10-20)

| Compound No. | $LD_{50}$ (mg/kg) | $ED_{50}$ (mg/kg) | TI |
|---|---|---|---|
| 15 | 48.4 (44.1-54.2) | 2.0 (1.8-2.3) | 24 |
| 16 | 46.5 (42.7-50.7) | 2.0 (1.8-2.3) | 23 |
| Etomidate | 50.3 (46.6-55.8) | 2.0 (1.8-2.3) | 25 |

Conclusion: the etomidate derivative of the present invention achieves an anesthetic effect in mice, and the anesthetic efficacy is close to etomidate.

Experimental Example 2

Test of the etomidate derivative of the present invention for latent period and persistent period of anesthesia in mice Male Kunming mice were divided into groups, 5 for each group. The test drug was administered by injection at a constant rate via caudal vein for 10 seconds. The time for disappearance of righting reflex (latent period) and the time for recovery (persistent period) were recorded.

The test results of latent period and persistent period of anesthesia of the compounds in mice are listed in Table 2:

TABLE 2

Test results of latent period and persistent period of anesthesia of the compounds (mice, mg/kg, n = 5)

| Compound No. | Dosage (mg/kg) | Latent period (s) | Persistent period (s) | Walking time (s) |
|---|---|---|---|---|
| 15 | 6 (3*$ED_{50}$) | 5.90 ± 0.88 | 83.60 ± 29.13 | 68.80 ± 30.10 |
| 16 | 6 (3*$ED_{50}$) | 5.80 ± 0.79 | 82.10 ± 20.18 | 98.10 ± 63.96 |
| Etomidate | 6 (3*$ED_{50}$) | 5.40 ± 0.52 | 175.50 ± 100.09 | 156.30 ± 120.78 |

Conclusion: the etomidate derivative of the present invention achieves an anesthetic effect close to etomidate, together with a rapid onset and a short duration of action.

In addition, the inventor also found that in mice anesthesia test, the compounds of the present invention had a minor influence on the blood pressure and followed-up reactions after recovery in mice. The data are listed in Table 3:

TABLE 3

Influence of the compounds on the blood pressure and followed-up reactions after recovery in mice

| Compound No. | After administration & Before anesthesia | | | | | Post-recovery | | |
|---|---|---|---|---|---|---|---|---|
| | tremor (%) | grooming (%) | tail bleeding (%) | | | quiet (%) | convulsion (%) | jump (%) |
| | | | none | few | much | | | |
| 15 | 70 | — | 10 | 50 | 40 | 100 | — | — |
| 16 | 70 | 10 | 10 | 60 | 30 | 80 | — | 20 |
| Etomidate | 80 | 20 | 40 | 50 | 10 | 50 | 10 | 40 |

Experimental Example 3

Test of the degree of inhibition to the corticosterone secretion in rats by the etomidate derivative of the present invention The degree of inhibition to the corticosterone secretion in rats by the etomidate derivative of the present invention was assessed according to the method described in *Anesthesiolgy* 2010; 112 (3): 637-644, using etomidate as a positive control.

Experimental Method:

Rats were recovered for 1 day with catheterization, and divided into groups (6 for negative control group, 8 for each of the remaining groups). Then 0.2 mg/kg of dexamethasone (concentration 0.04 mg/mL, administration volume 5 mL/kg) was administered by injection via caudal vein. After 2 hours, blood samples were collected through carotid arteries, and baseline values of serum corticosterone were determined ($C_{0min}$ of corticosterone, negative control). Then, 0.2 mg/kg of dexamethasone, compound 15, compound 16 and etomidate (positive control) were administered, respectively, immediately followed by administration of 25 μg/kg of $ACTH_{1-24}$ (concentration 5 μg/mL, administration volume 5 mL/kg) by injection via caudal vein. After 15 minutes, blood samples were collected through carotid arteries, and the concentrations of corticosterone were determined ($C_{15min}$ of corticosterone). The test results are listed in Table 4:

TABLE 4

The degree of inhibition to the corticosterone secretion in rats by the etomidate derivative of the present invention

| Compound No. | Dosage (mg/kg) | $C_{0\,min}$ of corticosterone (ng/ml) | $C_{15\,min}$ of corticosterone (ng/ml) |
|---|---|---|---|
| Compound 15 | 4 | 8.135 ± 3.985 | 115.320 ± 11.407**# |
| Compound 16 | 4 | 6.530 ± 3.733 | 88.762 ± 10.939*# |
| Positive control | 4 | 2.775 ± 0.383 | 19.464 ± 1.856* |
| Negative control | NA | 3.580 ± 0.749 | 57.990 ± 12.129 |

Compared to the negative control group,
*P < 0.05,
**P < 0.001;
Compared to the positive control group,
P < 0.001.

From the above results, it can be seen that the etomidate derivative of the present invention shows no inhibition of the secretion of corticosteroids in rat.

To sum up, the compound of the present invention not only has advantages similar to etomidate (i.e., having good anesthetic activity, rapid onset, and short duration of action, with little influence on the cardiovascular system), but also shows no inhibition to the secretion of cortisol and/or corticosterone, and therefore has both favorable anesthetic effect and safety profiles.

What is claimed is:

1. An etomidate derivative of Formula 1:

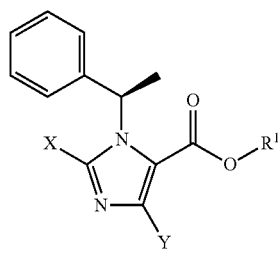

Formula 1 wherein,

X and Y are independently halogen or hydrogen, with the proviso that X and Y are not hydrogen at the same time; and $R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl, or a pharmaceutically acceptable salt, a polymorph, or a solvate thereof.

2. The etomidate derivative according to claim 1, selected from the group consisting of:

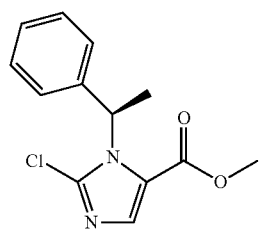

Compound 1

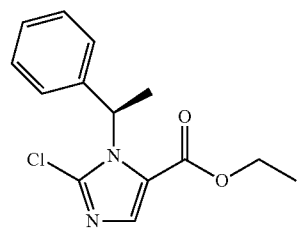

Compound 2

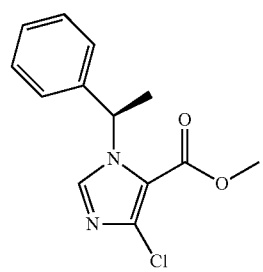

Compound 3

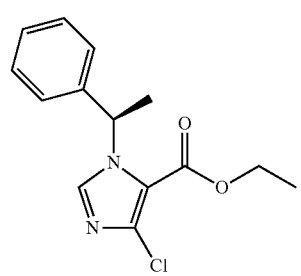

Compound 4

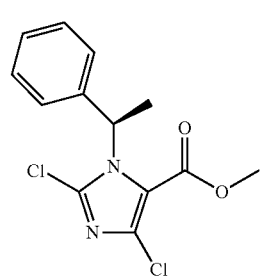

Compound 5

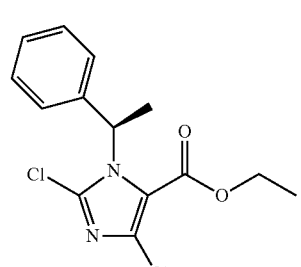

Compound 6

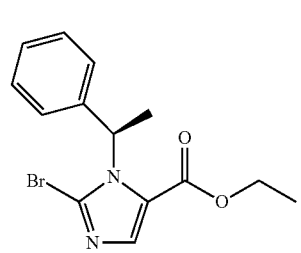

Compound 7

-continued
Compound 8
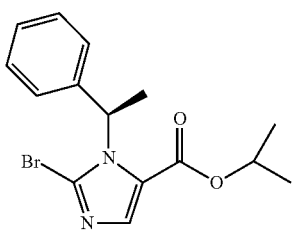
Compound 9
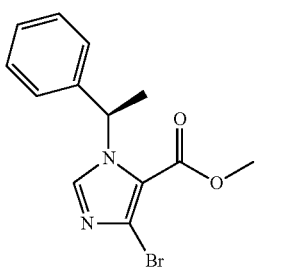
Compound 10
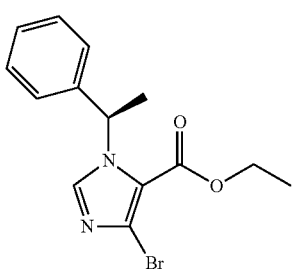
Compound 11
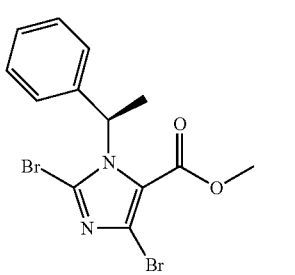
Compound 12
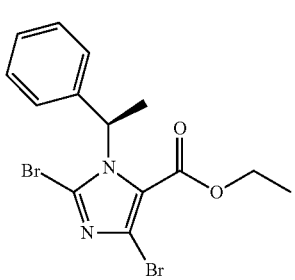
Compound 13
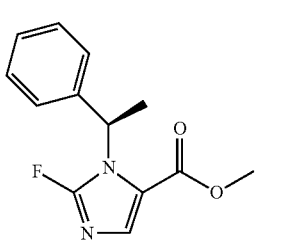
-continued
Compound 14
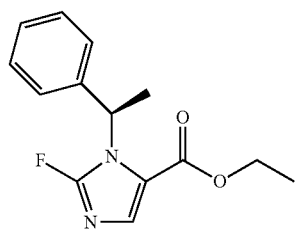
Compound 15
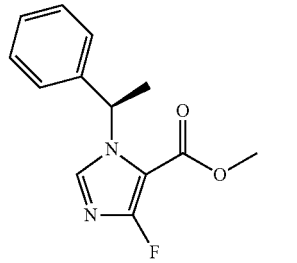
Compound 16
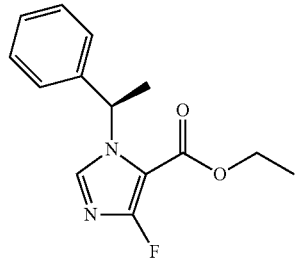
Compound 17
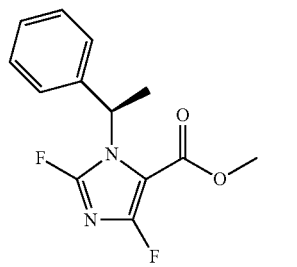
Compound 18
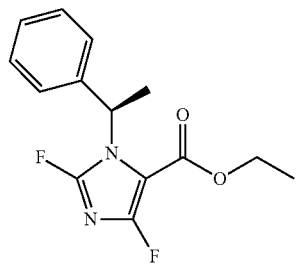
Compound 19
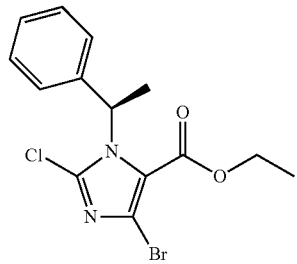

-continued

Compound 20

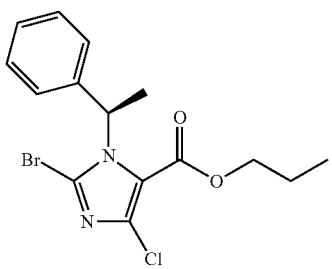

Compound 21

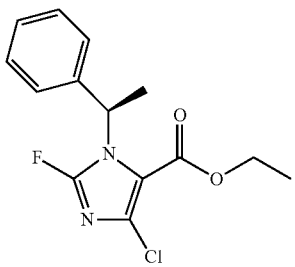

Compound 22

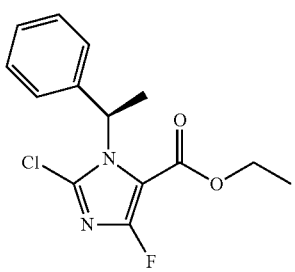

Compound 23

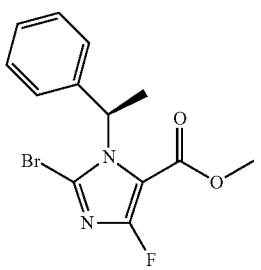

Compound 24

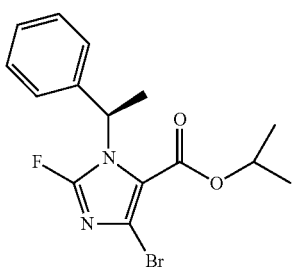

Compound 25

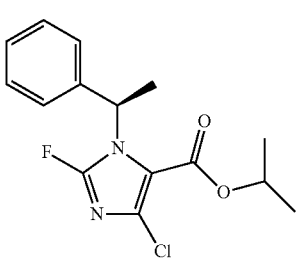

-continued

Compound 26

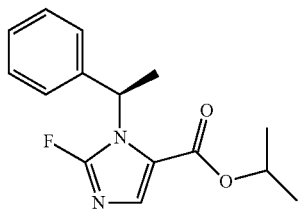

Compound 27

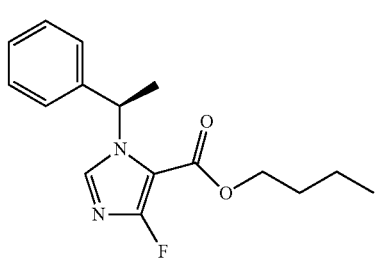

Compound 28

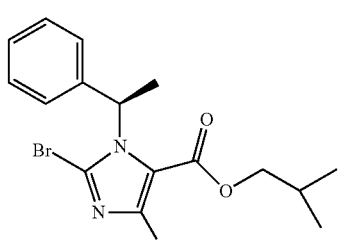

Compound 29

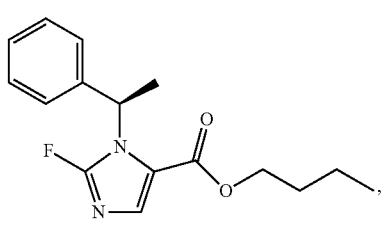

or a pharmaceutically acceptable salt, a polymorph, or a solvate thereof.

3. A pharmaceutical composition comprising the etomidate derivative according to claim 1, or a pharmaceutically acceptable salt, a polymorph, or a solvate thereof, and one or more pharmaceutically acceptable carriers.

4. A kit comprising the etomidate derivative according to claim 1, or a pharmaceutically acceptable salt, a polymorph, or a solvate thereof, or the pharmaceutical composition according to claim 3.

5. An anesthetic method, comprising administration of effective amount of the etomidate derivative according to claim 1 or a pharmaceutically acceptable salt, a polymorph or a solvate thereof to an animal in need thereof.

6. A method for preparing the etomidate derivative according to claim 1, including:

preparing the etomidate derivative from a compound of Formula 2:

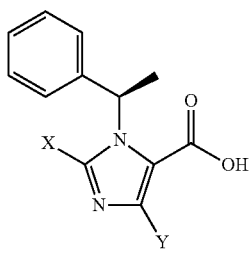

Formula 2 wherein,

X and Y are independently halogen or hydrogen, with the proviso that X and Y are not hydrogen at the same time.

7. The method according to claim 6, wherein the compound of Formula 2 is selected from the group consisting of:

Compound 30

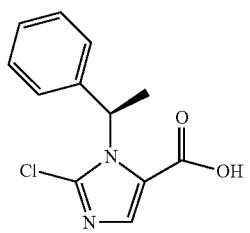

Compound 31

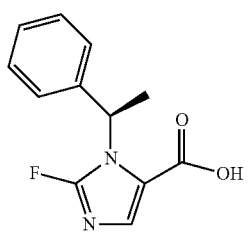

Compound 32

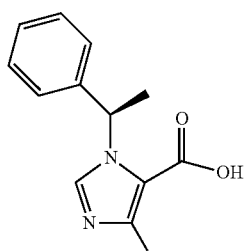

Compound 33

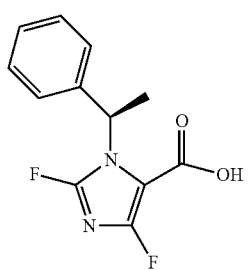

Compound 34

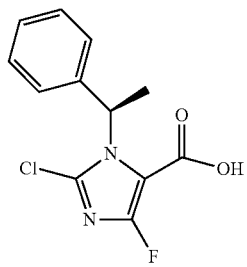

Compound 35

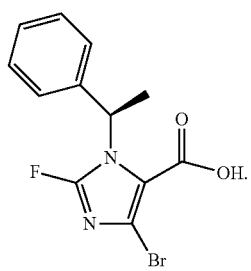

8. A compound of Formula 2:

Formula 2

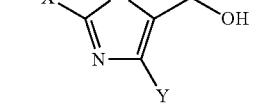

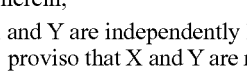

wherein,

X and Y are independently halogen or hydrogen, with the proviso that X and Y are not hydrogen at the same time, or a salt, a polymorph, or a solvate thereof.

9. The compound of Formula 2 according to claim 8, selected from the group consisting of:

Compound 30

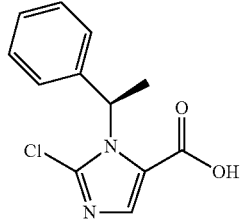

Compound 31

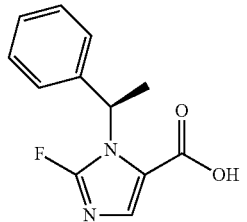

-continued

Compound 32

Compound 33

Compound 34

Compound 35 or a salt, a polymorph, or a solvate thereof.

10. A method for preparing the etomidate derivative according to claim 1, including:
preparing the etomidate derivative from a compound of Formula 3:

Formula 3 wherein,
X and Y are independently halogen or hydrogen, with the proviso that X and Y are not hydrogen at the same time; and
$R^1$ is $C_{1-6}$ alkyl, $C_{2-6}$ alkenyl, $C_{2-6}$ alkynyl, $C_{3-6}$ cycloalkyl or $C_{6-10}$ aryl, optionally substituted with one or more substituents selected from the group consisting of halogen, hydroxyl, amino, cyano, $C_{1-6}$ alkoxyl, $C_{2-7}$ alkoxycarbonyl, $C_{3-6}$ cycloalkyl and $C_{6-10}$ aryl.

11. The method according to claim 10, wherein the compound of Formula 3 is selected from the group consisting of:

Compound 36

Compound 37

Compound 38

Compound 39

Compound 40

Compound 41

Compound 42

Compound 43

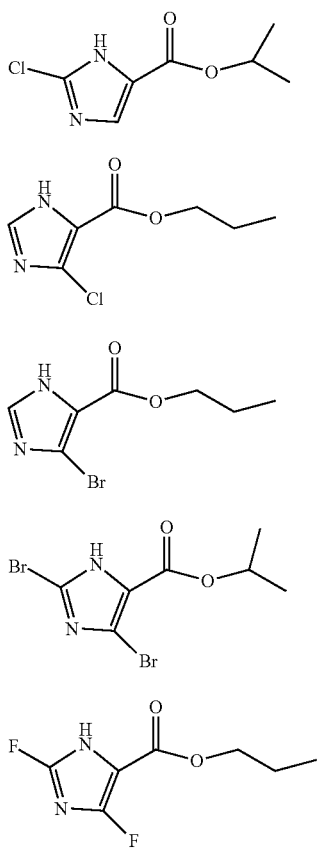

Compound 44

Compound 45

Compound 46

Compound 47

Compound 48

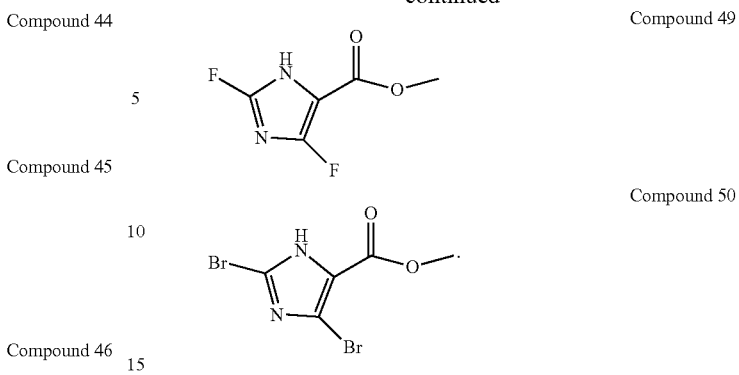

Compound 49

Compound 50

12. The etomidate derivative according to claim 1, wherein the halogen of X and Y is fluorine, chlorine or bromine.

13. The etomidate derivative according to claim 1, wherein $R^1$ is $C_{1-6}$ alkyl.

14. The etomidate derivative according to claim 13, wherein $R^1$ is methyl, ethyl, propyl, isopropyl, n-butyl or isobutyl.

15. The method according to claim 6, wherein the halogen of X and Y is fluorine, chlorine or bromine.

16. The compound according to claim 8, wherein the halogen is fluorine, chlorine or bromine.

17. The method according to claim 10, wherein the halogen of X and Y is fluorine, chlorine or bromine.

18. The method according to claim 10, wherein $R^1$ is $C_{1-6}$ alkyl.

19. The method according to claim 18, wherein $R^1$ is methyl, ethyl, propyl, isopropyl, n-butyl or isobutyl.

\* \* \* \* \*